(12) United States Patent
Nakayama (10) Patent No.: US 10,335,112 B2
(45) Date of Patent: Jul. 2, 2019

(54) X-RAY CT APPARATUS AND CONTROL METHOD FOR THE X-RAY CT APPARATUS

(71) Applicant: HITACHI, LTD., Tokyo (JP)

(72) Inventor: Masato Nakayama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 274 days.

(21) Appl. No.: 15/535,625

(22) PCT Filed: Jan. 18, 2016

(86) PCT No.: PCT/JP2016/051198
§ 371 (c)(1),
(2) Date: Jun. 13, 2017

(87) PCT Pub. No.: WO2016/121543
PCT Pub. Date: Aug. 4, 2016

(65) Prior Publication Data
US 2018/0103924 A1 Apr. 19, 2018

(30) Foreign Application Priority Data

Jan. 27, 2015 (JP) .................................. 2015-013275

(51) Int. Cl.
*G01T 1/166* (2006.01)
*A61B 6/03* (2006.01)
(Continued)

(52) U.S. Cl.
CPC .............. *A61B 6/585* (2013.01); *A61B 6/032* (2013.01); *A61B 6/488* (2013.01); *A61B 6/54* (2013.01);
(Continued)

(58) Field of Classification Search
CPC ....... A61B 6/482; A61B 6/037; A61B 6/4241; A61B 6/032; A61B 6/04; A61B 6/40;
(Continued)

(56) References Cited

U.S. PATENT DOCUMENTS 5,740,222 A 4/1998 Fujita et al.
5,748,696 A 5/1998 Fujita et al.
(Continued)

FOREIGN PATENT DOCUMENTS

JP 5-269117 10/1993
JP 7-148149 6/1995
(Continued)

OTHER PUBLICATIONS

International Search Report dated Apr. 19, 2016 in connection with PCT/JP2016/051198.

*Primary Examiner* — Don K Wong
(74) *Attorney, Agent, or Firm* — Cooper & Dunham LLP (57) ABSTRACT

In order to appropriately reduce time until scanning can be started after preparation in both an operation console and a scan room is completed, an X-ray CT apparatus includes an X-ray tube, an X-ray detector, a rotation disk, an image calculation device, a display device, a system control device, an operation console instruction device that instructs the system control device to prepare, start, and stop scanning in an operation console, and a scan gantry instruction device that instructs the system control device to prepare, start, and stop scanning in a scan room, in which the system control device includes a scanning preparation control unit that performs some scanning preparation processes among a plurality of scanning preparation processes on the basis of an instruction for scanning preparation from the operation console instruction device or the scan gantry instruction device.

8 Claims, 11 Drawing Sheets

(51) Int. Cl.
*H02K 15/02* (2006.01)
*A61B 6/00* (2006.01)
*G01N 23/046* (2018.01)

(52) U.S. Cl.
CPC ............ *G01N 23/046* (2013.01); *A61B 6/545* (2013.01); *A61B 6/583* (2013.01); *G01N 2223/419* (2013.01)

(58) Field of Classification Search
CPC ... A61B 6/42; A61B 6/46; G06T 2207/10081; G06T 2207/10116; G06T 2207/10141; G06T 2211/428; G06T 2211/412
See application file for complete search history.

(56) References Cited

U.S. PATENT DOCUMENTS

| | | | |
|---|---|---|---|
| 5,848,126 | A | 12/1998 | Fujita et al. |
| 2007/0058771 | A1* | 3/2007 | Sauer .................... G06T 11/005 378/4 |
| 2011/0116598 | A1 | 5/2011 | Gotman et al. |
| 2013/0044856 | A1 | 2/2013 | Gotman et al. |

FOREIGN PATENT DOCUMENTS

| | | |
|---|---|---|
| JP | 9-308626 | 12/1997 |
| JP | 2011-529764 | 12/2011 |

* cited by examiner

| OPERATION | SIGNAL A | SIGNAL B |
|---|---|---|
| PRESSING OF OPERATION CONSOLE SCANNING PREPARATION BUTTON | ON | – |
| PRESSING OF OPERATION CONSOLE STOPPING BUTTON | OFF | – |
| PRESSING OF SCAN GANTRY SCANNING PREPARATION BUTTON | – | ON |
| PRESSING OF SCAN GANTRY STOPPING BUTTON | – | OFF |

(b)

| | | SIGNAL B | |
|---|---|---|---|
| | | OFF | ON |
| SIGNAL A | OFF | State1 | State3 |
| | ON | State2 | State4 |

(c)

| | | SIGNAL B | | | |
|---|---|---|---|---|---|
| | | OFF | | ON | |
| | | Signal1 | Signal3 | Signal1 | Signal3 |
| | | ON | OFF | OFF | ON |
| | OFF | Signal2 | Signal4 | Signal2 | Signal4 |
| | | OFF | OFF | OFF | OFF |
| SIGNAL A | | Signal1 | Signal3 | Signal1 | Signal3 |
| | | OFF | OFF | OFF | OFF |
| | ON | Signal2 | Signal4 | Signal2 | Signal4 |
| | | ON | OFF | OFF | ON |

$Signal1 = \overline{A} \cdot \overline{B}$
$Signal2 = A \cdot (A \oplus B)$
$Signal3 = B \cdot (A \oplus B)$
$Signal4 = A \cdot B$

FIG.4A

✔ : EXECUTABLE, – : NON-EXECUTABLE

| PROCESSING DEVICE | SCANNING PREPARATION PROCESS | State 1 | State 2 | State 3 | State 4 |
|---|---|---|---|---|---|
| GANTRY CONTROL DEVICE | SETTING OF X-RAY IRRADIATION WIDTH OF COLLIMATOR (MEASUREMENT SLICE THICKNESS) | – | ✔ | – | ✔ |
| | INCLINATION OF ROTATION DISK (IMAGING ANGLE) | – | – | – | ✔ |
| | LOW SPEED ROTATION OF ROTATION DISK (OTHER THAN SCANOGRAM) | – | ✔ | – | ✔ |
| | HIGH SPEED ROTATION OF ROTATION DISK (SCANNING ROTATION SPEED) | – | – | – | ✔ |
| | MOVEMENT OF X-RAY TUBE POSITION (SCANOGRAM SCANNING DIRECTION) | – | ✔ | – | ✔ |
| | ⋮ | | | | |
| BED CONTROL DEVICE | MOVEMENT OF TOP PLATE LONGITUDINAL DIRECTION POSITION (SCANNING STARTING POSITION) | – | – | – | ✔ |
| | SETTING OF TOP PLATE MOVEMENT SPEED (HELICAL PITCH OF HELICAL SCANNING) | – | ✔ | – | ✔ |
| | SETTING TOP PLATE MOVEMENT DISTANCE (MOVEMENT DISTANCE PER SCANNING OF AXIAL SCANNING) | – | ✔ | – | ✔ |
| | ⋮ | | | | |
| X-RAY CONTROL DEVICE | HEATING OF CATHODE OF X-RAY TUBE (TUBE CURRENT) | – | – | – | ✔ |
| | LOW SPEED ROTATION OF ANODE OF X-RAY TUBE (TUBE CURRENT) | – | ✔ | ✔ | ✔ |
| | HIGH SPEED ROTATION OF ANODE OF X-RAY TUBE (TUBE CURRENT) | – | – | – | ✔ |
| | ⋮ | | | | |
| IMAGE CALCULATION DEVICE | SETTING OF IMAGE CALCULATION CONDITIONS (IMAGE SLICE THICKNESS, PRESENCE OR ABSENCE OF VARIOUS CORRECTIONS, AND THE LIKE) | – | ✔ | – | ✔ |
| | SWITCHING TO SCANNING MODE (TEMPORARY STOPPING OF IMAGE CALCULATION) | – | – | – | ✔ |
| | ⋮ | | | | |
| STORAGE DEVICE | RESERVATION OF COLLECTED DATA STORAGE REGION (NUMBER OF SCANNINGS) | – | ✔ | – | ✔ |
| | RESERVATION OF IMAGE DATA STORAGE REGION (NUMBER OF CT IMAGES) | – | ✔ | – | ✔ |
| | ⋮ | | | | |

FIG.4B

| ✔ : EXECUTABLE, – : NON-EXECUTABLE | | State | | | |
|---|---|---|---|---|---|
| PROCESSING DEVICE | SCANNING PREPARATION PROCESS | 1 | 2 | 3 | 4 |
| DISPLAY DEVICE | SWITCHING TO SCANNING IMAGE DISPLAY MODE | – | – | – | ✔ |
|  | : |  |  |  |  |
| OPERATION CONSOLE INSTRUCTION DEVICE | INVALIDATION OF OPERATION CONSOLE BED MOVEMENT BUTTON | – | – | ✔ | ✔ |
|  | (BLINKING OF OPERATION CONSOLE SCANNING PREPARATION BUTTON) | – | – | ✔ | – |
|  | : |  |  |  |  |
| SCAN GANTRY INSTRUCTION DEVICE | INVALIDATION OF SCAN GANTRY BED MOVEMENT BUTTON | – | – | ✔ | ✔ |
|  | INVALIDATION OF SCAN GANTRY ROTATION DISK INCLINATION BUTTON | – | – | ✔ | ✔ |
|  | (BLINKING OF SCAN GANTRY SCANNING PREPARATION BUTTON) | – | ✔ | – | – |
|  | : |  |  |  |  |

|  | SIGNAL A | SIGNAL B |
|---|---|---|
| PRESSING OF OPERATION CONSOLE SCANNING PREPARATION BUTTON | ON | – |
| PRESSING OF OPERATION CONSOLE STOPPING BUTTON | OFF | OFF |
| PRESSING OF OPERATION CONSOLE SCAN GANTRY SCANNING PREPARATION BUTTON | – | ON |
| PRESSING OF SCAN GANTRY SCANNING PREPARATION BUTTON | – | ON |
| PRESSING OF SCAN GANTRY STOPPING BUTTON | – | OFF |

| OPERATION | SCANNING PREPARATION MODE |
|---|---|
| SWITCHING USING OPERATION CONSOLE SCANNING PREPARATION MODE SWITCH | SINGLE-PERSON MODE |
|  | TWO-PERSON MODE |

(b)

| OPERATION | SIGNAL A | SIGNAL B |
|---|---|---|
| PRESSING OF OPERATION CONSOLE SCANNING PREPARATION BUTTON | ON | ON |
| PRESSING OF OPERATION CONSOLE STOPPING BUTTON | OFF | OFF |
| PRESSING OF SCAN GANTRY SCANNING PREPARATION BUTTON | – | ON |
| PRESSING OF SCAN GANTRY STOPPING BUTTON | – | OFF |

(c)

| OPERATION | SIGNAL A | SIGNAL B |
|---|---|---|
| PRESSING OF OPERATION CONSOLE SCANNING PREPARATION BUTTON | ON | – |
| PRESSING OF OPERATION CONSOLE STOPPING BUTTON | OFF | – |
| PRESSING OF SCAN GANTRY SCANNING PREPARATION BUTTON | – | ON |
| PRESSING OF SCAN GANTRY STOPPING BUTTON | – | OFF |

| PRIORITY CONDITIONS {SCANNING PREPARATION MODE SWITCHING CONDITION, PART, SCANNING PROTOCOL} | SWITCHING CHECKING MESSAGE DISPLAY |
|---|---|
| SCANNING PREPARATION MODE SWITCHING CONDITION {OFF, ON} | ON |

(b)

| SCANNING PREPARATION MODE SWITCHING CONDITION | SINGLE-PERSON MODE | TWO-PERSON MODE |
|---|---|---|
| NUMBER OF INPUT OF EXAMINER NAMES {O OR LESS, O OR MORE} | ✓ 1 OR LESS | ✓ 2 OR MORE |
| INITIAL SCANNING IN EXAMINATION | ☐ | ☐ |
| SCANNING METHOD | ☐ | ✓ |
| SCANOGRAM | ☐ | ✓ |
| AXIAL | ☐ | ☐ |
| HELICAL | ☐ | ☐ |
| ELECTROCARDIOGRAPHIC SYNCHRONOUS | ☐ | ✓ |
| ADDITIONAL SCANNING | ✓ | ☐ |
| RE-SCANNING | ☐ | ✓ |
| SCANOGRAM PLAN {ABSENCE, PRESENCE} | ☐ | ✓ ABSENCE |
| CONTRAST AGENT INJECTION {ABSENCE, PRESENCE} | ☐ | ✓ PRESENCE |
| *2 | ☐ | ✓ 500 mm OR MORE |
| GANTRY INCLINATION {ABSENCE, PRESENCE} | ☐ | ✓ PRESENCE |
| : | | |

(c)

| PART | SCANNING PREPARATION MODE SETTING |
|---|---|
| CHEST | SINGLE-PERSON MODE |
| ABDOMEN | TWO-PERSON MODE |
| : | : |

(d)

| SCANNING PROTOCOL | SCANNING PREPARATION MODE SETTING |
|---|---|
| A | SINGLE-PERSON MODE |
| B | TWO-PERSON MODE |
| : | : |

(e)

PERFORM SCANNING PREPARATION PROCESS IN O-PERSON MODE. ARE YOU SURE?

YES    NO

*2: MOVEMENT DISTANCE TO SCANNING STARTING POSITION {OO mm OR LESS, OO mm OR MORE}

X-RAY CT APPARATUS AND CONTROL METHOD FOR THE X-RAY CT APPARATUS

TECHNICAL FIELD

The present invention relates to an X-ray CT apparatus and the like, and particularly to scanning preparation control for an X-ray CT apparatus in a scan room.

BACKGROUND ART

An X-ray CT apparatus, which includes an X-ray source which irradiates an object with X-rays and an X-ray detector which detects a dose of X-rays transmitted through the object as projection data, reconstructs a tomographic image of the object by using pieces of projection data from a plurality of angles obtained by rotating the X-ray source and the X-ray detector around the object, and displays the reconstructed tomographic image. An image displayed by the X-ray CT apparatus draws a shape of an organ of an object, and is used for image diagnosis.

Various conditions such as a range of a tomographic image of an object to be obtained, and a method of obtaining projection data by rotating a rotation disk at a predetermined speed under a predetermined X-ray condition, are set on an operation console in advance, the X-ray CT apparatus transitions to a state in which scanning can be started on the basis of the conditions, then controls a scan gantry in a scan room so as to obtain a tomographic image, and displays the tomographic image.

In examination using an X-ray CT apparatus, as a method for increasing the number of examinations, there is a method in which two operators respectively located at an operation console and in a scan room perform examination. In this use method, particularly, in contrast scanning examination requiring the care of an object (securing of a contrast agent injection route), there are many cases where the X-ray CT apparatus starts scanning while checking a situation of a contrast agent injection route in the object, and thus it is useful that there is means for bringing the X-ray CT apparatus into a state in which scanning can be performed from the scan room.

For example, PTL 1 discloses a method in which an operation console which plans scanning conditions and a scanning range and a scan room which takes care of an object independently generate signals at the time when preparation is completed, and transition to a state in which scanning can be started at the time when both of the signals are provided.

CITATION LIST

Patent Literature

PTL 1: Japanese Patent No. 3685546

SUMMARY OF INVENTION

Technical Problem

However, in order for an X-ray CT apparatus to actually start scanning, the X-ray CT apparatus is required to satisfy various conditions in which a rotation disk reaches a predetermined rotation speed, a cathode of an X-ray tube reaches a desired temperature, a rotation anode of the X-ray tube reaches a predetermined rotation speed, a top plate of a bed is placed at a predetermined position in a longitudinal direction, the rotation disk is inclined at a predetermined angle, and an image calculation device is ready to generate an image according to image calculation conditions.

For example, as disclosed in PTL 1, if both of the operation console and the scan room complete preparation and then transition to a state in which scanning can be started, it takes time to satisfy various conditions for a state in which scanning can be started.

On the other hand, in a case where the X-ray CT apparatus starts scanning while checking a situation of an object in the scan room, a position of the top plate of the bed in the longitudinal direction is required to be moved according to a situation of the object, and thus a state is preferable in which the bed can be moved up to right before scanning is started in the scan room. If image calculation under different conditions for examination or image calculation for another object is performed by the image calculation device, a calculation process is preferably continued to be performed up to right before scanning is started. Therefore, it is necessary to reduce time required for the X-ray CT apparatus to be able to start scanning by taking into consideration a situation of an operation of the X-ray CT apparatus being necessary, improvement of processing performance, and service life of a wearing component.

The present invention has been made in consideration of the above-described problems, and an object thereof is to provide an X-ray CT apparatus and the like which can appropriately reduce time until scanning can be started after both of an operation console and a scan room complete preparation.

Solution to Problem

In order to achieve the above-described object, according to the present invention, there is provided an X-ray CT apparatus including an X-ray source that irradiates an object, with X-rays; an X-ray detector that is disposed to oppose the X-ray source and detects X-rays having been transmitted through the object; a rotation disk that is mounted with the X-ray source and the X-ray detector, and is rotated around the object; an image reconstruction device that reconstructs a tomographic image of the object, on the basis of a transmitted X-ray dose detected by the X-ray detector; an image display device that displays the tomographic image reconstructed by the image reconstruction device; a system control device that controls the respective devices so as to perform scanning; an operation console instruction device that instructs the system control device to prepare, start, and stop scanning in an operation console; and a scan gantry instruction device that instructs the system control device to prepare, start, and stop scanning in a scan room, in which the system control device includes a scanning preparation control unit that performs some scanning preparation processes among a plurality of scanning preparation processes on the basis of an instruction for scanning preparation from the operation console instruction device or the scan gantry instruction device.

There is provided a control, method for an X-ray CT apparatus including an X-ray source that irradiates an object with X-rays, an X-ray detector that is disposed to oppose the X-ray source and detects X-rays having been transmitted through the object, a rotation disk that is mounted with the X-ray source and the X-ray detector, and is rotated around the object, an image reconstruction device that reconstructs a tomographic image of the object on the basis of a transmitted X-ray dose detected by the X-ray detector, an image display device that displays the tomographic image reconstructed by the image reconstruction device, a system control device that controls the respective devices so as to perform scanning, an operation console instruction device that instructs the system control device to prepare, start, and stop scanning in an operation console, and a scan gantry instruction device that instructs the system control device to prepare, start, and stop scanning in a scan room, the method including causing the system control device to perform some scanning preparation processes among a plurality of scanning preparation processes on the basis of an instruction for scanning preparation from the operation console instruction device or the scan gantry instruction device.

Advantageous Effects of Invention

According to the present invention, it is possible to provide an X-ray CT apparatus and the like which can appropriately reduce time until scanning can be started after both of an operation console and a scan room complete preparation,

DESCRIPTION OF EMBODIMENTS

Figure 1:
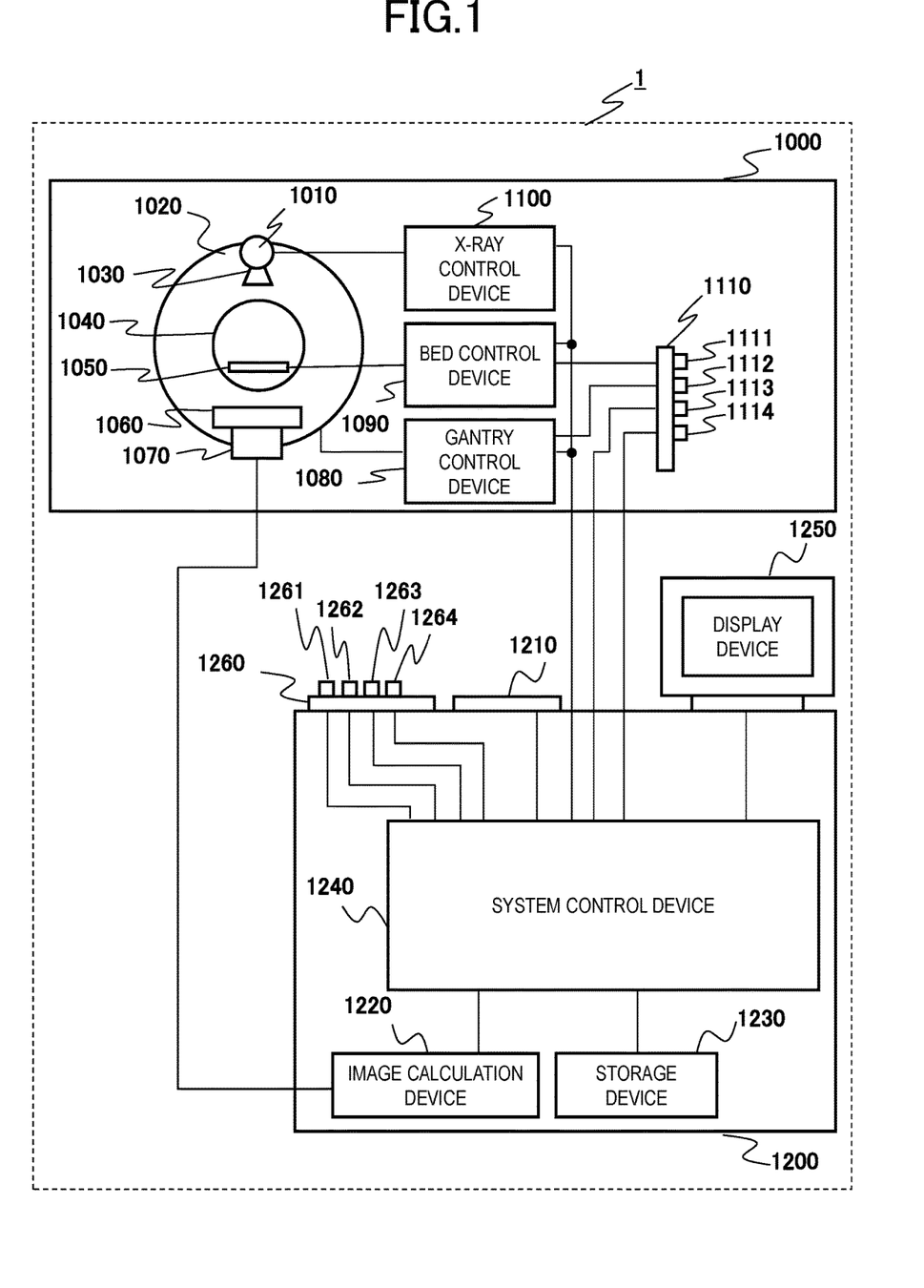
FIG. 1 is a diagram illustrating a schematic configuration of an X-ray CT apparatus.
Figure 2:
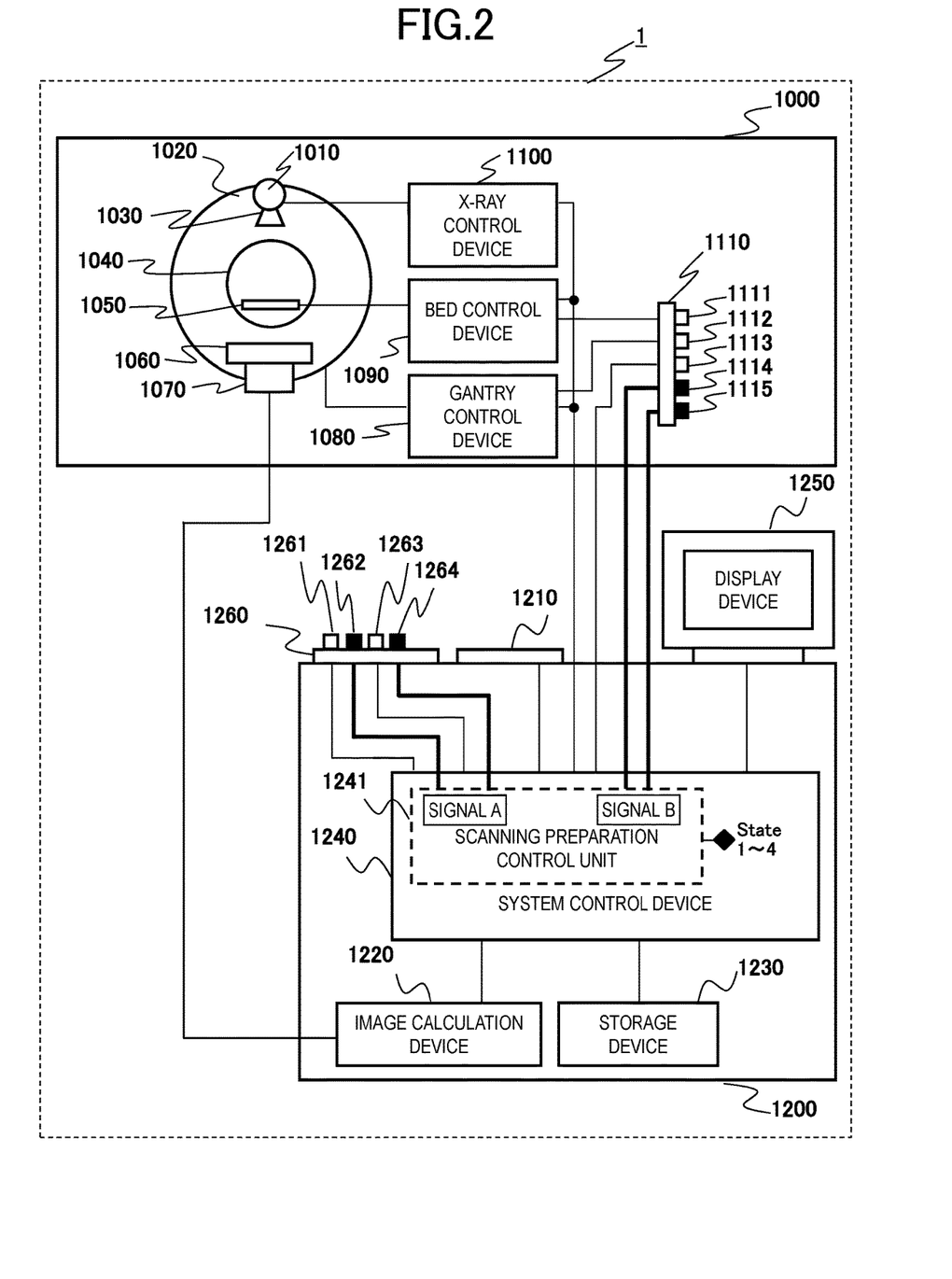
FIG. 2 is a diagram illustrating a schematic configuration of an X-ray CT apparatus in a first embodiment.

Hereinafter, with reference to the drawings, each embodiment of the present invention will be described. First, with reference to FIG. 1, a summary of an X-ray CT apparatus 1 common to all embodiments will be described. As illustrated in FIG. 1, the X-ray CT apparatus 1 includes a scan gantry portion 1000 and an operation console 1200.

The scan gantry portion 1000 includes an X-ray tube 1010, a rotation disk 1020, a collimator 1030, an X-ray detector 1060, a data collecting device 1070, a bed 1050, a gantry control device 1080, a bed control device 1090, an X-ray control device 1100, and a scan gantry instruction device 1110.

The X-ray tube 1010 is a device which irradiates an object mounted on the bed 1050 with X-rays.

The collimator 1030 is a device which restricts an irradiation range of X-rays applied from the X-ray tube 1010. The rotation disk 1020 is provided with an opening 1040 into which the object mounted on the bed 1050 is inserted, and is also mounted with the X-ray tube 1010 and the X-ray detector 1060 so as to rotate the X-ray tube 1010 and the X-ray detector 1060 around the object. The X-ray detector 1060 is a device which is disposed to oppose the X-ray tube 1010, and detects X-rays having been transmitted through the object so as to measure a spatial distribution of the transmitted X-rays. The X-ray detector 1060 may be formed by arranging a plurality of X-ray detection elements in a one-dimensional manner in a rotation direction of the rotation disk 1020 or arranging a plurality of X-ray detection elements in a two-dimensional manner in a rotation direction and a rotation axis direction of the rotation disk 1020.

The data collecting device 1070 is a device which collects an X-ray dose detected by the X-ray detector 1060 as digital data. The gantry control device 1080 is a device which controls rotation and inclination of the rotation disk 1020, and an X-ray irradiation width of the collimator 1030. The bed control device 1090 is a device which controls movement of the bed 1050 in an upward-and-downward direction and a front-and-rear direction. The X-ray control device 1100 is a device which controls power which is input to the X-ray tube 1010.

The scan gantry instruction device 1110 includes a scan gantry bed movement button 1111, a scan gantry rotation disk inclination button 1112, a scan gantry scanning starting button 1113, and a scan gantry stopping button 1114, and is a device which directly gives an instruction to the bed control device 1090 and the gantry control device 1080 without using a system control device 1240 so as to give an instruction for upward-and-downward and front-and-rear movements of the bed 1050 and an inclination of the rotation disk 1020, gives an instruction for starting and stopping of scanning via the system control device, and is specifically hard buttons.

The operation console 1200 includes an input device 1210, an image calculation device 1220, a display device 1250, a storage device 1230, a system control device 1240, and an operation console instruction device 1260. The input device 1210 is a device used to input an object name, an examination number, scanning conditions, and the like, and is, specifically, a keyboard or a pointing device. The image calculation device 1220 is a device which performs a calculation process on measured data sent from the data collecting device 1070 so as to reconstruct a CT image. The display device 1250 is a device which displays an object name, the examination number, scanning conditions, and the like which are input via the input device 1210, and a CT image or the like created by the image calculation device 1220, and is, specifically, a cathode-ray tube (CRT), a liquid crystal display, or the like.

The storage device 1230 is a device which stores data collected toy the data collecting device 1070, and image data of a CT image created by the image calculation device 1220, and is, specifically, a hard disk, drive (HDD), or the like.

The system control device 1240 is a device which controls the above-described devices, the gantry control device 1080, the bed control device 1090, and the X-ray control device 1100 of the scan gantry portion 1000, so as to perform scanning and front-and-rear movement, of the bed 1050 in the operation console 1200. The operation console instruction device 1260 includes an operation console bed movement button 1261, an operation console scanning preparation button 1262, an operation console scanning starting button 1263, and an operation console stopping button 1264, and is a device which gives an instruction for front-and-rear movement of the bed 1050, scanning preparation, scanning starting and stopping, and the like via the system control device, and is, specifically, hard buttons, or graphical user interface (GUI) buttons displayed on the display device 1250.

The X-ray control device 1100 controls power which is input, to the X-ray tube 1010 via the system control device 1240 through an operation on the operation console scanning preparation button 1262 and the operation console scanning starting button 1263 of the operation console instruction device 1260 on the basis of scanning conditions which are input from the input device 1210, particularly, an X-ray tube voltage or an X-ray tube current, and the X-ray tube 1010 irradiates an object with X-rays corresponding to the scanning conditions. The X-ray detector 1060 detects X-rays which are applied from the X-ray tube 1010 and are transmitted through the object by using a plurality of X-ray detection elements, and thus detects a distribution of the transmitted X-rays. The rotation disk 1020 is controlled by the gantry control device 1080, and is rotated on the basis of scanning conditions which are input from the input device 1210, especially, a rotation speed and the like. The bed 1050 is controlled by the bed control device 1090, and is operated on the basis of scanning conditions which are input from the input device 1210, especially, a spiral pitch and the like.

X-ray irradiation from the X-ray tube 1010 and measurement of a transmitted X-ray distribution performed by the X-ray detector 1060 are repeatedly performed along with rotation of the rotation disk 1020, and thus projection data from various angles is acquired. The acquired projection data from various angles is transmitted to the image calculation device 1220. The image calculation device 1220 performs an back projection process on the transmitted projection data from various angles so as to reconstruct, a CT image. The reconstructed CT image is displayed on the display device 1250.

First Embodiment

With reference to FIGS. 2 to 5, a description will be made of a first embodiment of the present invention. In an X-ray CT apparatus 1 illustrated in FIG. 2, the system control device 1240 includes a scanning preparation control unit 1241 as an internal processing unit of the first embodiment, and the scan gantry instruction device 1110 includes a scan gantry scanning preparation button 1115. The scanning preparation control unit 1241 is configured by installing dedicated software in the system control device 1240. Hereinafter, the same constituent, elements as those in FIG. 1 are given the same reference numerals, and repeated description will be omitted.

Figure 3:
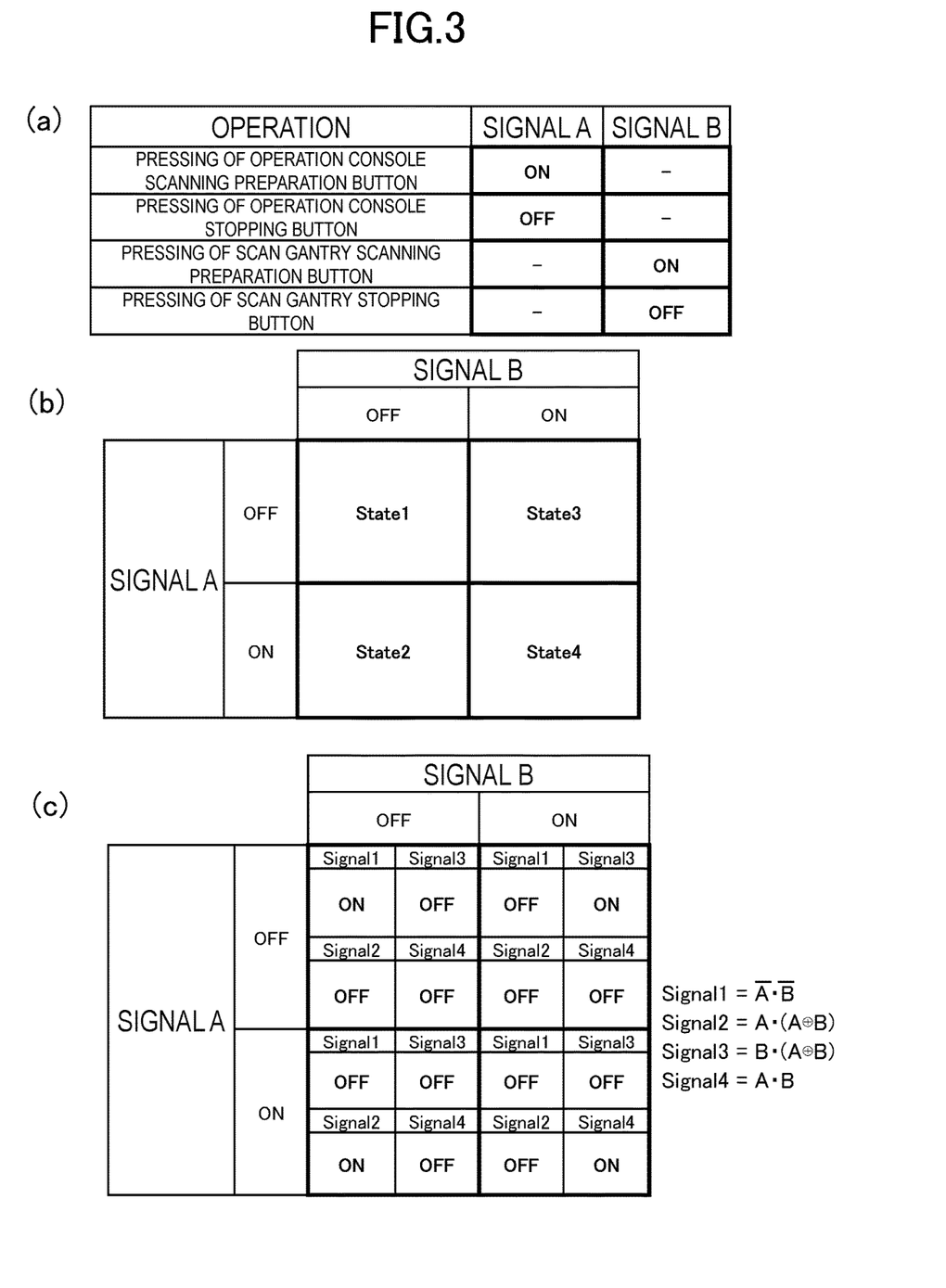
FIG. 3 is a diagram illustrating a process in a scanning preparation control unit in the first embodiment.

The scanning preparation control unit 1241 generates two signals A and B through four button operations such as pressing of the operation console scanning preparation button 1262, pressing of the operation console stopping button 1264, pressing of the scan gantry scanning preparation button 1115, and pressing of the scan gantry stopping button 1114, as illustrated in FIG. 3(a), and has four states, that is, State1 (A=OFF, B=OFF), State2 (A=ON, B=OFF), State3 (A=OFF, B=ON), and State4 (A=ON, B=ON) with the two signals A and B as inputs, as illustrated in FIG. 3(b). As illustrated in FIG. 3(c), these four states may be obtained on the basis of four logic calculation results, that is, Signal1=AND(NOT(A),NOT(B)), Signal2=AND(A,XOR (A, B)), Signal3=AMD(B,XOR(A,B)), Signal4=AND (A, B) with the two signals A and B as inputs. Here, NOT(•) indicates logical negation, AND(•,•) indicates logical product, and XOR(•,•) indicates exclusive sum.

Figure 4A:
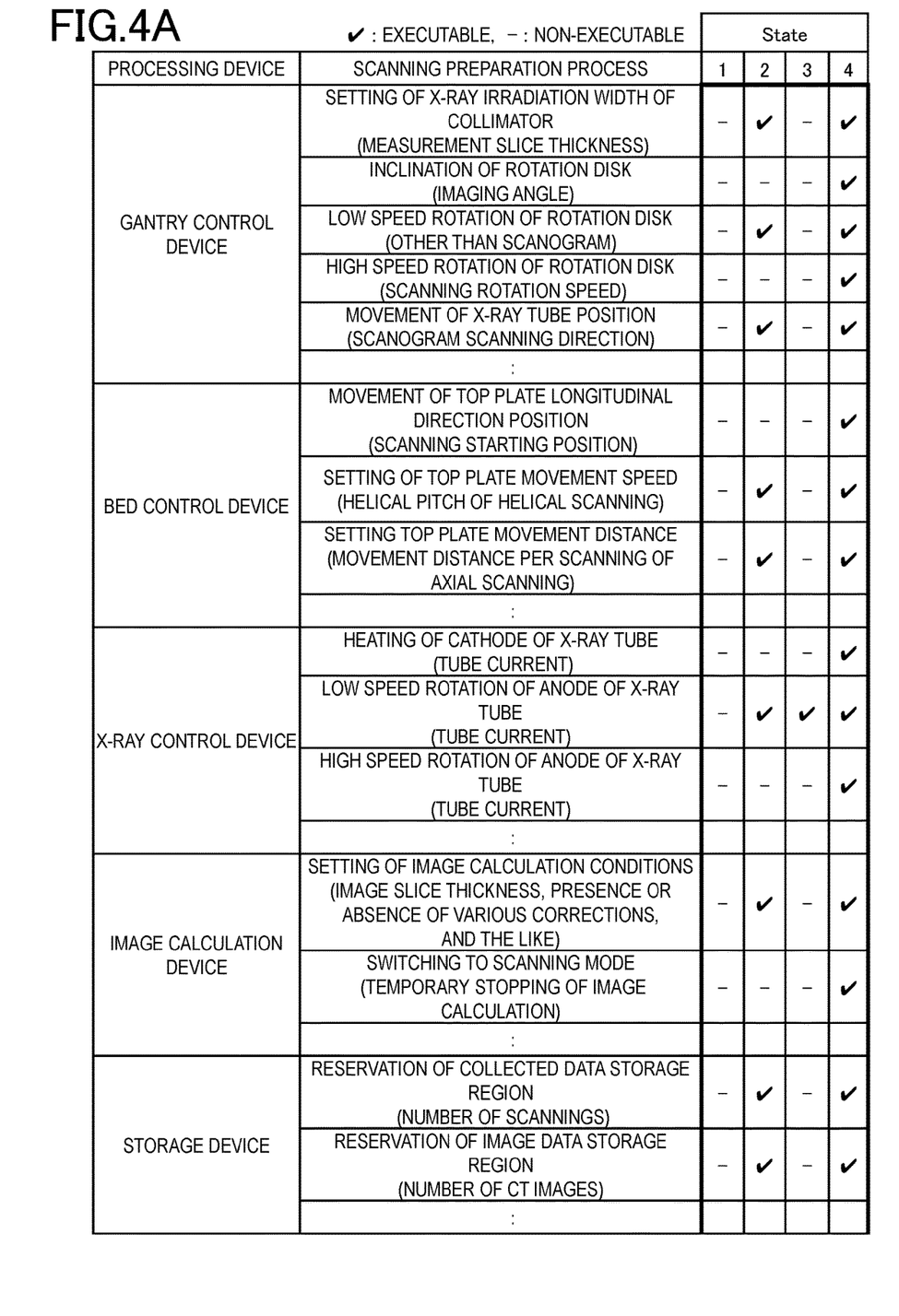
FIG. 4A is a diagram illustrating a scanning preparation control table in the first embodiment.
Figure 4B:
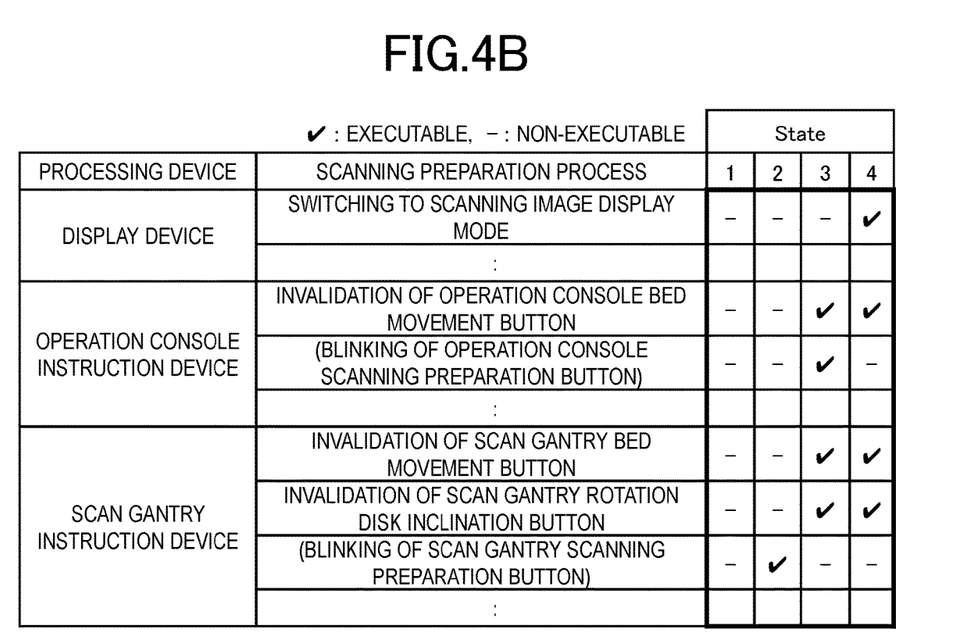
FIG. 4B is a diagram illustrating a scanning preparation control table in the first embodiment.

FIG. 4A and FIG. 4B illustrate examples of a scanning preparation control table illustrating a relationship between a predetermined processing device and a scanning preparation process which can be performed by the processing device in the four states (States1 to State4). Here, "√" indicates an executable state, and "–" indicates a non-executable state. The scanning preparation control unit 1241 controls a scanning preparation process on the basis of the scanning preparation control table and the present state which is output with the two signals A and B as inputs.

In this scanning preparation control table, a scanning preparation process to be performed on the basis of scanning conditions (a scanning type such as scanogram, helical, or axial, or measurement slice thickness) set by the operation console 1200 is performed in a state of State2 in which the operation console scanning preparation button 1262 is pressed. On the other hand, a scanning preparation process having no relation to scanning conditions set by the operation console 1200, for example, a low speed rotation of the anode of the X-ray tube 1010 is defined to be performed in a state of State3 in which the scan gantry scanning preparation button 1115 is pressed.

A scanning preparation process related to the service life of a wearing component, for example, a high speed rotation of the rotation disk 1020 or heating of the cathode and a high speed rotation of the anode of the X-ray tube 1010 are defined to be performed in a state of State4 in which both of the operation console scanning preparation button 1262 and the scan gantry scanning preparation button 1115 are pressed.

A scanning preparation process related to a throughput (improvement of processing performance), for example, switching (reconstruction calculation temporary stoppage) to a scanning mode of the image calculation device 1220 is also defined to be performed in a state of State4.

On the basis of the scanning preparation control table defined in the above-described way, for example, in a case where the present state is State2, the scanning preparation control unit 1241 causes the gantry control device 1080 to set an X-ray irradiation width of the collimator and to rotate the rotation disk 1020 at a low speed, and similarly causes respective processing devices such as the bed control device 1090 and the X-ray control device 1100 to perform, executable scanning preparation processes in State2.

If a state of State2 transitions to a state of State4 as a result of the scan gantry scanning preparation button 1115 being pressed, the scanning preparation control unit 1241 causes each processing device to perform a process which is not performed excluding the process which has already been performed in State2, among scanning preparation processes which can be performed in State4.

Here, in a case where a state of State4 is returned to a state of State2 as a result of the scan gantry stopping button 1114 being pressed, the scanning preparation control unit 1241 makes only processes which can be executed in a state of State2 valid, and causes the respective processing devices to cancel other scanning preparation processes, on the basis of the scanning preparation control table illustrated in FIG. 4A and FIG. 4B.

A scanning preparation process performed in each processing device includes a general protection process, for example, automatic cancelation after a predefined time elapses. For example, in a case where a process related to the service life of a wearing component is canceled among the scanning preparation processes which are performed in a state of State2 or State3, the scanning preparation control unit 1241 holds the state of State2 or State3, and performs control so that a process which is automatically canceled is performed again in a stage of having transitioned to State4. If there is any scanning preparation process which is automatically canceled in a state of State4, transition to State1 occurs, and all scanning preparation processes are canceled.

The scanning preparation control unit 1241 may perform determination on the basis of not only the scanning preparation control table illustrated in 4A and FIG. 4B and the present state which is output with the two signals A and B as inputs, but also conditions for performing other scanning preparation processes, for example, whether or not object information is input, and an accumulated heat quantity of X-rays exceeding 100% even though scanning is performed under set scanning conditions.

Figure 5:
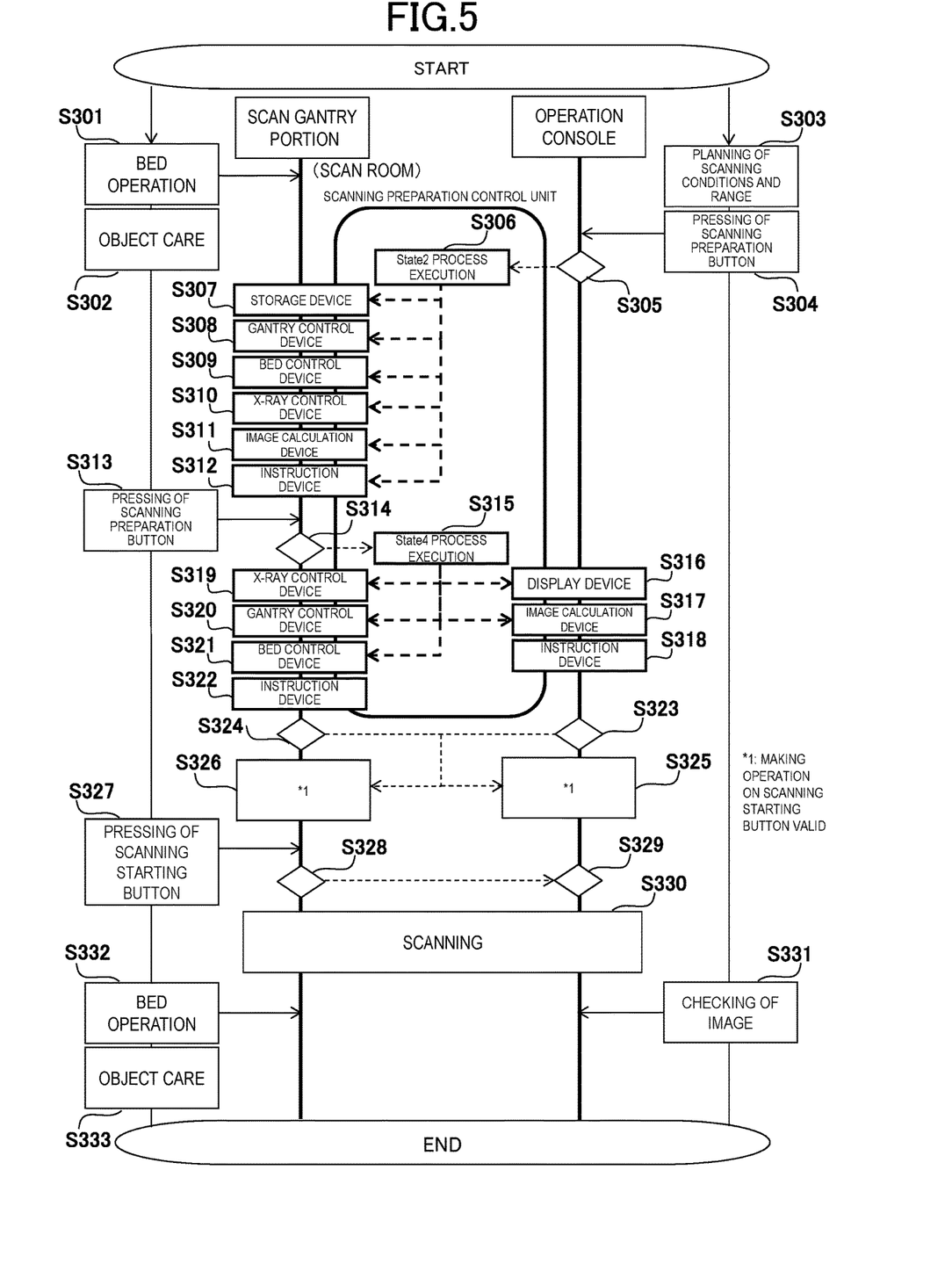
FIG. 5 is a flowchart illustrating a flow of an operation and a process in the first embodiment.

FIG. 5 illustrates an example of an examination flow capable of effectively using the X-ray CT apparatus 1 in the first embodiment, and illustrates a flow in which a contrast scanning examination following simple scanning is performed by two operators located at the operation console and in the scan room.

First, in S301, the bed 1050 is moved to a position where work is easily performed in order to secure a route (blood vessel) into which a contrast agent is injected in an object, mounted on the bed 1050 of the scan room, and, in S302, the care of the object (securing of a contrast, agent injection route) is taken.

Along with the work in the scan room, in the operation console 1200, in S303, scanning conditions for contrast examination and a scanning range are planned and set, then, in S304, the operation console scanning preparation button 1262 is pressed, and, in S305, the scanning conditions and the scanning range are transmitted to the system control device 1240.

Here, since a state of State2 occurs in which the signal A is ON, and the signal B is OFF, the scanning preparation control unit 1241 performs scanning preparation processes which can be performed in State2 illustrated in FIG. 4A and FIG. 4B in S306.

Specifically, the scanning preparation control unit 1241 causes the storage device 1230 to reserve a collected data storage region and an image data storage region in S307, and causes the gantry control device 1080 to set an X-ray irradiation width, of the collimator 1030 and to perform a low speed rotation of the rotation disk 1020 in S308. The scanning preparation control unit 1241 causes the bed control device 1090 to set a top plate movement speed for helical scanning in S309, causes the X-ray control device 1100 to perform a low speed rotation of the anode of the X-ray tube 1010 in S310, and causes the image calculation device 1220 to set image calculation conditions in S311. Since these processes are performed, it is possible to reduce scanning preparation process time required after the scan gantry scanning preparation button 1115 is pressed.

In a state of State2, the image calculation device 1220 is not temporarily stopped for scanning, and can thus continue to perform image calculation under other conditions for simple scanning or image calculation for other objects. The scanning preparation control unit 1241 causes the scan gantry instruction device 1110 to perform, for example, blinking of the scan gantry scanning preparation button 1115, and can thus clearly show that the scanning preparation process is performed in the operation console 1200 (S312).

In the scan room, if the care of the object is completed, and the operator in the scan room confirms that the scanning preparation process in the operation console is performed, the scan gantry scanning preparation button 1115 is pressed in S313, thus a state of State4 occurs in which the signal A is ON, and the signal B is ON in S314, and thus scanning preparation processes which can be performed in State4 illustrated in FIG. 4A and FIG. 4B are performed in S315.

Here, among the scanning preparation processes which can be performed in State4, only processes which have not been performed in the state of State2 are performed. Specifically, in the operation console 1200, the scanning preparation control unit 1241 causes the display device 1250 to switch to a scanning image display mode in S316, causes the image calculation device 1220 to temporarily stop currently performed image calculation, in order to allocate, for example, only one system for scanning if there are two systems of calculation units, and to allocate a single system for scanning if there is the single system of a calculation unit in S317, and causes the operation console instruction device 1260 to invalidate the operation console bed movement button 1261 in S318.

In the scan gantry portion 1000, the scanning preparation control unit 1241 causes the X-ray control device 1100 to perform heating of the cathode and a high speed rotation of the anode of the X-ray tube 1010 in S319, causes the gantry control device 1080 to perform a high speed rotation of the rotation disk 1020 at a scanning rotation speed in S320, causes the bed control device 1090 to move a position of the top plate in the longitudinal direction to a scanning starting position in S321, and causes the scan gantry instruction device 1110 to invalidate the scan gantry bed movement button 1111 and the scan gantry rotation disk inclination button 1112 in S322.

If it is determined that the scanning preparation processes are completed in S323 and S324, the scanning preparation control unit 1241 makes an operation on the operation console scanning starting button 1263 of the operation console 1200 valid in S325, and makes an operation on the scan gantry scanning starting button 1113 of the scan gantry portion 1000 valid in S326.

As mentioned above, in the operation console 1200 and the scan room located at separated positions, since some scanning preparation processes can be precedingly started in a stage in which scanning conditions and a scanning range are fixed, it is possible to reduce time until the X-ray CT apparatus 1 is brought into a state in which scanning can be started after preparation in the scan room is completed, and the scan gantry scanning preparation button 1115 is pressed.

In this stage, for example, in a case where an object's condition in the scan room changes, and the object's condition is desired to be checked by moving the top plate of the bed 1050, a state is returned from State4 to State2 by pressing the scan gantry stopping button 1114, and thus the scan gantry bed movement button 1111 can be operated. A necessary countermeasure is taken, and then a state transitions to State4 by pressing the scan gantry scanning preparation button 1115 again. If it is determined that necessary scanning preparation processes are completed in S323 and S324, the scanning preparation control unit 1241 causes an operation on the operation console scanning starting button 1263 of the operation console 1200 valid in S325, and causes an operation on the scan gantry scanning starting button 1113 of the scan gantry portion 1000 valid in S326.

If the scan gantry scanning starting button 1113 of the scan gantry portion 1000 is pressed in S327, the scan gantry portion 1000 notifies the operation console 1200 of scanning starting, and also makes the signal A and the signal B OFF so as to start scanning, in S328 and S329.

If the scanning is completed, in the operation console 1200, an image displayed on the display device 1250 is checked in S331. In the scan room, the bed 1050 is moved to a position where work is easily performed in S332, the care (detachment of a contrast agent injector) of the object is taken in S333, and the examination is finished.

As mentioned above, according to the X-ray CT apparatus 1 of the first embodiment, it is possible to appropriately reduce time until scanning can be started after preparation is completed in both of the operation console and the scan room. Particularly, the X-ray CT apparatus 1 of the first embodiment is optimal for a flow in which examination is performed by two operators in the operation console and the scan room.

Second Embodiment

Figure 6:
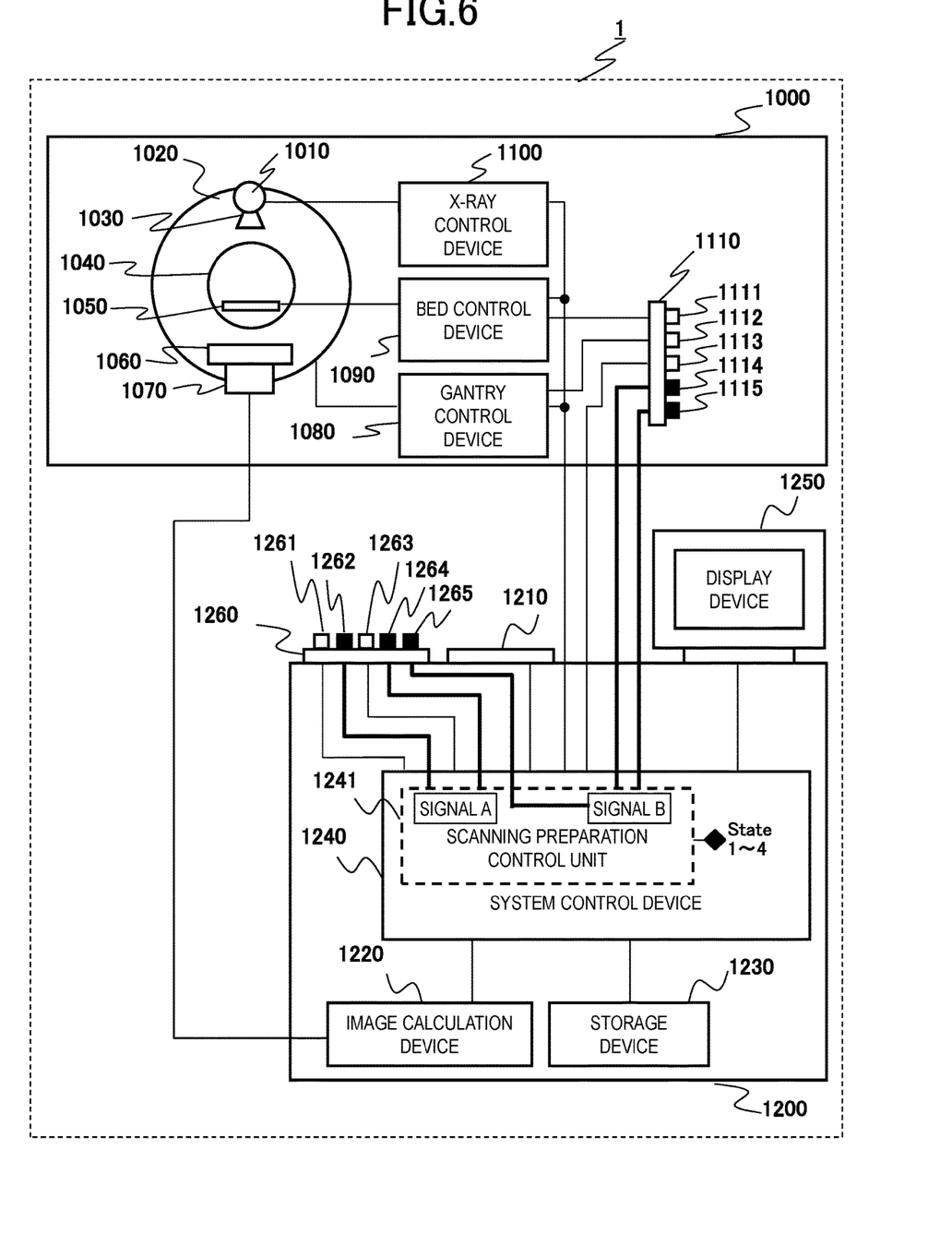
FIG. 6 is a diagram illustrating a schematic configuration of an X-ray CT apparatus in a second embodiment.
Figure 7:
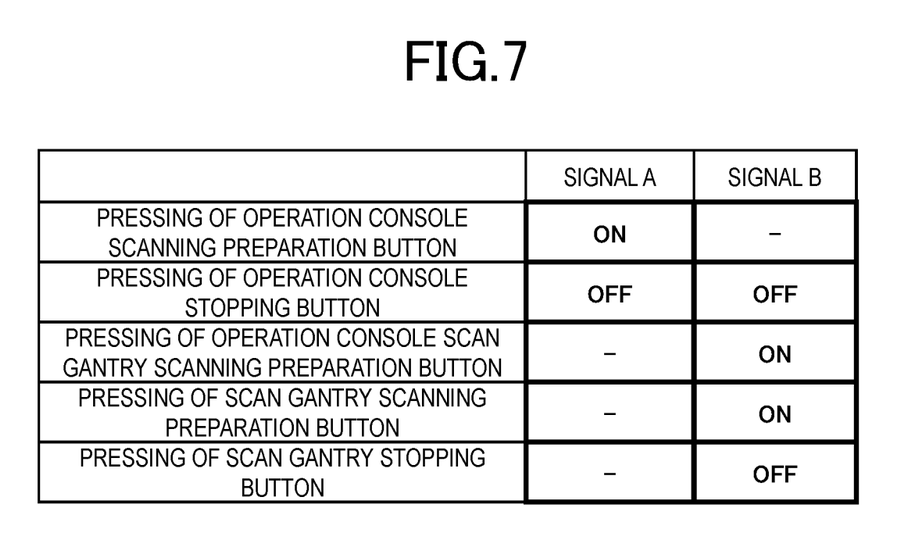
FIG. 7 is a diagram illustrating a process in a scanning preparation control unit in the second embodiment.

With reference to FIGS. 6 and 7, a second embodiment of the present invention will be described. For example, in a case where additional scanning is desired to be performed due to an insufficient scanning range, it is preferable to start scanning through an operation on only the operation console 1200 side without going to the scan room. Therefore, the X-ray CT apparatus 1 of the second embodiment has a configuration capable of coping with such a case.

In the X-ray CT apparatus 1 illustrated in FIG. 6, the system control device 1240 includes the scanning preparation control unit 1241 as an internal processing unit of the second embodiment, and the scan gantry instruction device 1110 includes the same scan gantry scanning preparation button 1115 as that in the first embodiment. The operation console instruction device 1260 includes an operation console scan gantry scanning preparation button 1265 having the same function as that of the scan gantry scanning preparation button 1115. Hereinafter, the same constituent elements as in FIGS. 1 and 2 are given the same reference numerals, and repeated description will be omitted.

As illustrated in FIG. 7, in the X-ray CT apparatus 1 of the second embodiment, two signals A and B are generated through a total of five button operations including an operation on the operation console scan gantry scanning preparation button 1265 in addition to four button operations in the first embodiment illustrated in FIG. 3(a).

If the operation console scan gantry scanning preparation button 1265 is pressed, the signal B is made ON in the same manner as in an operation of pressing the scan gantry scanning preparation button 1115. On the other hand, in a case of disposing a button on the operation console instruction device 1260, preferably, a button such as a stop button which can be used in common to respective operations is not provided in plurality.

An operator of the operation console 1200 may decide any order of transition to State2 and State3 by providing the operation console scan gantry scanning preparation button 1265. Therefore, an operation of canceling scanning preparation in the operation console is configured to be performed by using only the operation console stopping button 1264. In other words, in FIG. 7, if the operation console stopping button 1264 is pressed, the signals A and B are made OFF.

As a result, a state cannot transition from State4 to State3 in an operation on the operation console 1200, but, since most of the scanning preparation processes are performed in a state of State2 on the basis of scanning conditions set by using the operation console 1200, and a state can transition from State1 to State3 by pressing the operation console scan gantry scanning preparation button 1265 of the operation console 1200, it can be said that there is almost no influence on an operational aspect, even compared with the configuration of the first embodiment.

As a result, of employing such a configuration, in the X-ray CT apparatus 1 of the second embodiment, it is possible to complete a scanning preparation process without performing an operation in the scan room. In a flow in which two operators located at the operation console and in the scan room perform examination, it is possible to perform an operation equivalent to that in the X-ray CT apparatus 1 of the first embodiment.

Third Embodiment

Figure 8:
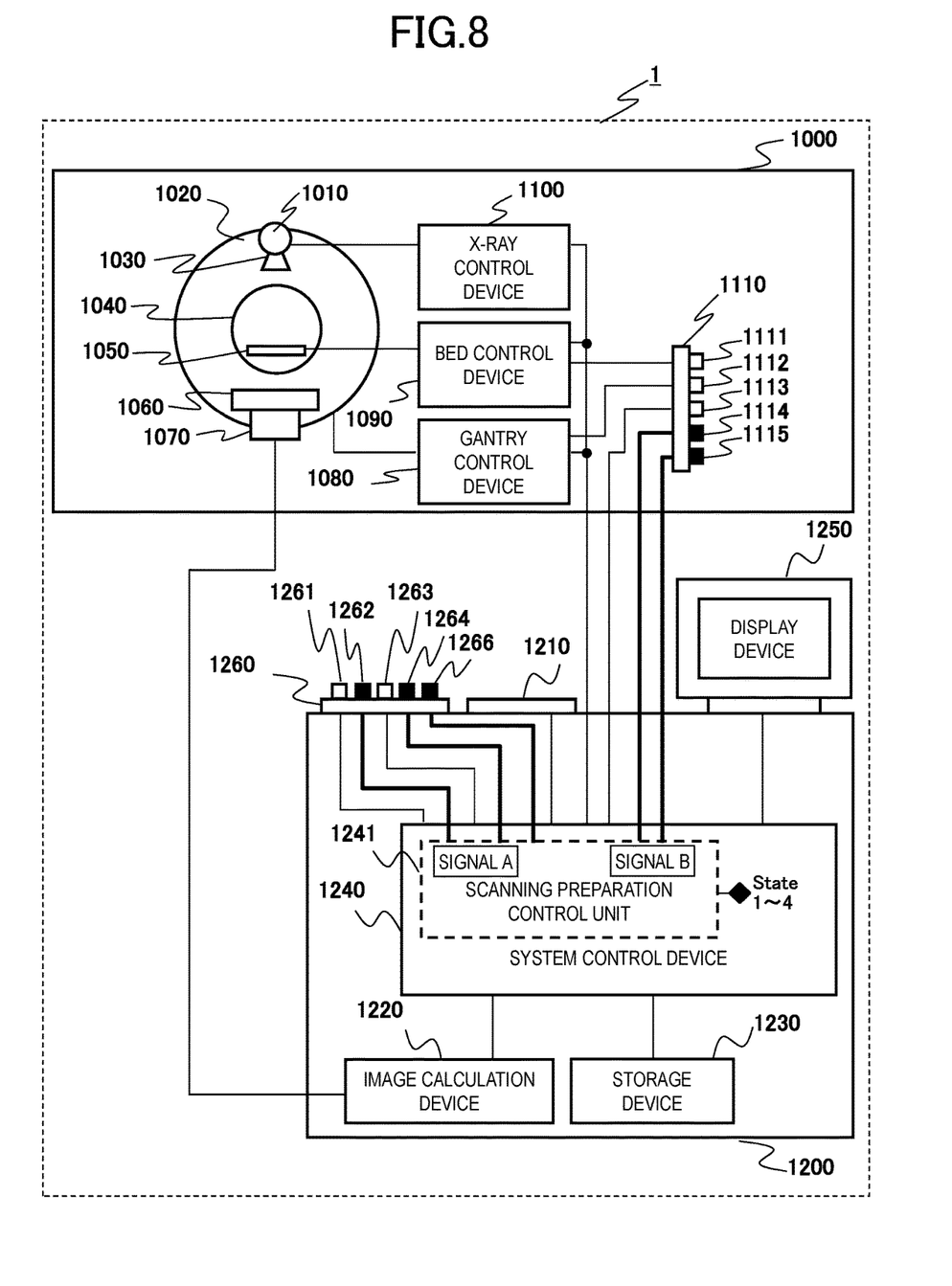
FIG. 8 is a diagram illustrating a schematic configuration of an X-ray CT apparatus in a third embodiment.
Figure 9:
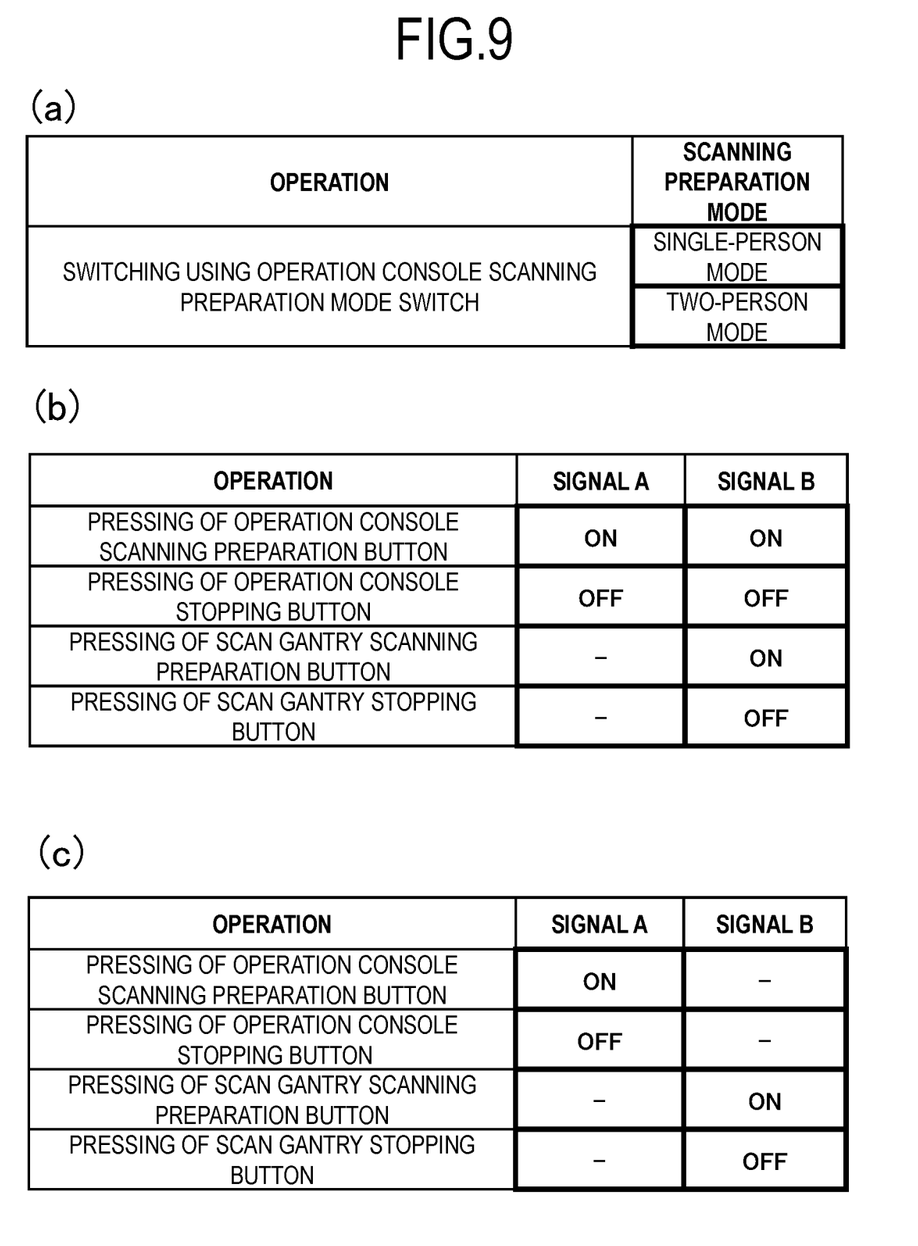
FIG. 9 is a diagram illustrating a process in a scanning preparation control unit in the third embodiment.
Figure 10:
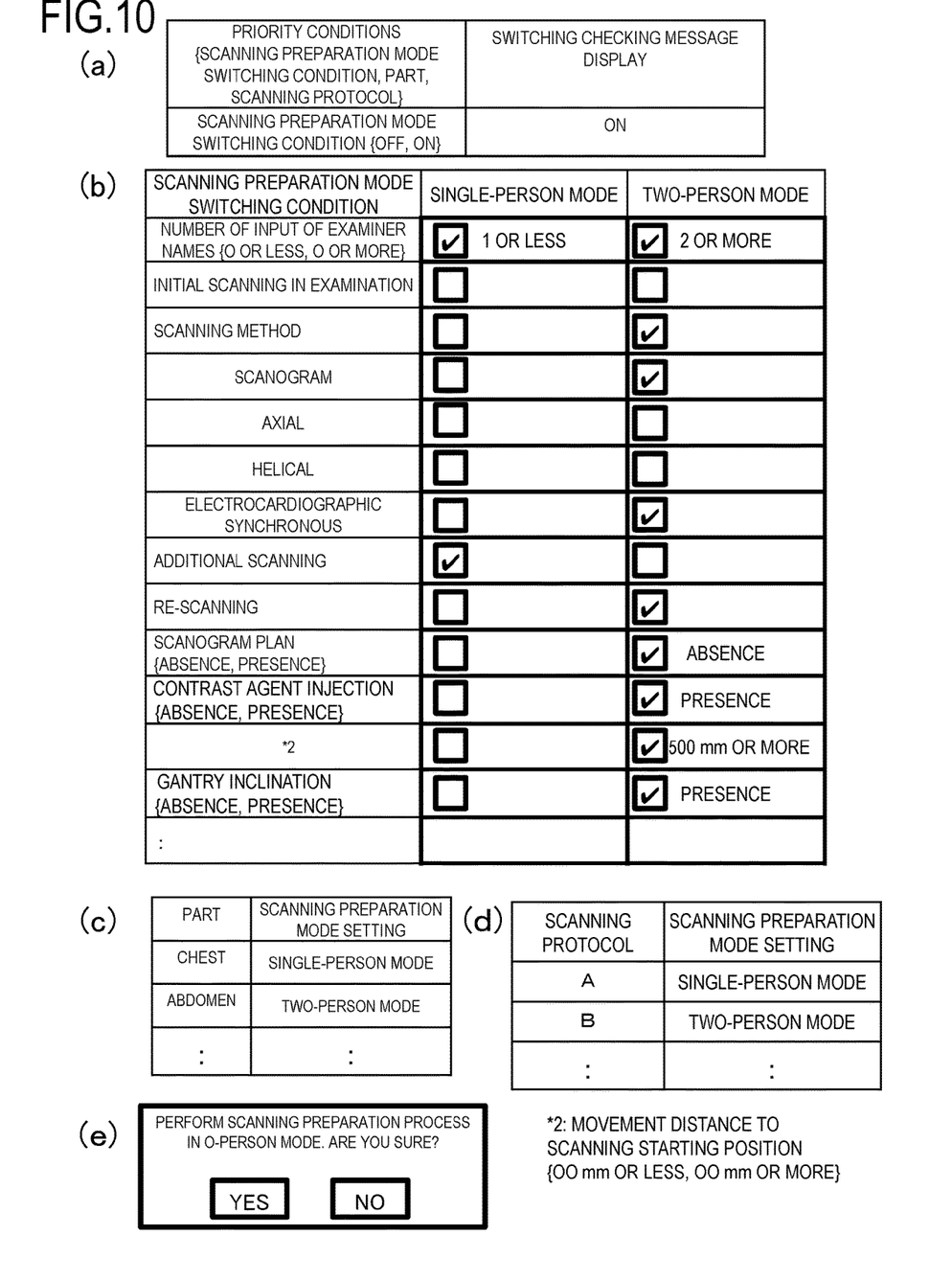
FIG. 10 is a diagram illustrating an automatic mode switching process in the third embodiment.

With reference to FIGS. 8 to 10, a description will be made of a third embodiment of the present, invention. In a facility where only one operator performs most of the examinations, it may be desirable to complete scanning preparation only by operating the operation console scanning preparation button 1262. Therefore, the X-ray CT apparatus 1 of the third embodiment has a configuration capable of coping with such a case.

In the X-ray CT apparatus 1 illustrated in FIG. 8, the system control device 1240 includes the scanning preparation control unit 1241 as an internal processing unit of the third embodiment, and the scan gantry instruction device 1110 includes the same scan gantry scanning preparation button 1115 as that in the first embodiment. The operation console instruction device 1260 includes an operation console scanning preparation mode switching switch 1266 instead of the operation console scan gantry scanning preparation button 1265. Hereinafter, the same constituent elements as in FIGS. 1, 2 and 6 are given the same reference numerals, and repeated description will be omitted.

As illustrated in FIGS. 9(a) to 9(c), the scanning preparation control unit 1241 switches between generation patterns of two signals A and B by using four button operations depending on whether the operation console scanning preparation mode switching switch 1266 is set to a single-person mode or a two-person mode.

In a case where a scanning preparation mode is a single-person mode, as illustrated in FIG. 9(b), both of the signals A and B are made ON by pressing the operation console scanning preparation button 1262, and both of the signals A and B are made OFF by pressing the operation console stopping button 1264. Only the signal B is made ON and OFF by pressing the scan gantry scanning preparation button 1115 and the scan gantry stopping button 1114, respectively.

A scanning preparation operation in the operation console 1200 is necessarily performed in order to set scanning conditions, a scanning range, and the like, and thus this operation is configured to complete and cancel scanning preparation.

On the other hand, in a case where a scanning preparation mode is the two-person mode, as illustrated in FIG. 9(c), the same operation as in FIG. 3(a) in the first embodiment is performed. In other words, only the signal A is made ON by pressing the operation console scanning preparation button 1262, and only the signal A is made OFF by pressing the operation console stopping button 1264. The signal B is made ON and OFF by pressing the scan gantry scanning preparation button 1115 and the scan gantry stopping button 1114, respectively.

This configuration can cope with both of a facility where a single person performs examination and a facility where two persons perform examination.

However, in an actual operation, there is a facility where it is determined whether a single person performs examination or two persons perform examination depending on the examination content. Therefore, there may be a configuration in which a normal operation is performed in a mode set in the operation console scanning preparation mode switching switch 1266, but, the scanning preparation control unit 1241 determines whether or not respective conditions (for example, the number of input examiner names, a scanning method, additional scanning, and whether or not a contrast agent is injected) set by an operator in advance are satisfied on the basis of a timing at which the operation console scanning preparation button 1262 is pressed, and if the conditions are satisfied, automatic switching to a designated (the other) mode is performed, or a message for checking switching to the designated (the other) mode is displayed (hereinafter, a switching process to the designated (the other) mode).

In "priority conditions {a scanning preparation mode switch condition, a part, and a scanning protocol}" illustrated in FIG. 10(a), there may be the designation of whether or not setting based on scanning preparation mode switching conditions illustrated in FIG. 10(b) is prioritized, whether or not setting of a scanning preparation mode set for each part illustrated in FIG. 10(c) is prioritized, or whether or not setting of a scanning preparation mode set for each scanning protocol illustrated in FIG. 10(d) is prioritized. Here, the scanning preparation mode switching conditions are defined according to scanning conditions other than the part and the scanning protocol.

In a case where setting based on the scanning preparation mode switching conditions is prioritized, the scanning preparation control unit 1241 performs the switching process to the designated (the other) mode if any one of the scanning preparation mode switching conditions is satisfied according to the table illustrated in FIG. 10(b).

For example, according to the setting of the "number of input examiner names {O or less, O or more}" illustrated in FIG. 10(b), the scanning preparation control unit 1241 performs a switching process to the "single-person mode" in a case where the number of input examiner names is one or less, and performs a switching process to the "two-person mode" in a case where the number of input examiner names is two or more.

For example, according to setting of a "scanning method (scanogram)" and a "scanning method (electrocardiographic synchronous)" illustrated in FIG. 10(b), the scanning preparation control unit 1241 performs a switching process to the "two-person mode" in a case where a scanning method is either of a scanogram method or an electrocardiographic synchronous method. Since checkboxes of the "scanning method" are in conjunction with checkboxes of "scanogram" to "electrocardiographic synchronous", if a check is input to the checkboxes of the "scanning method", a check can be input, to the checkboxes of "scanogram" to "electrocardiographic synchronous".

For example, according to setting of "additional scanning" illustrated in FIG. 10(b), the scanning preparation control unit 1241 performs a switching process to the "single-person mode" in a case of additional scanning.

For example, according to the setting of "re-scanning", "scanogram plan {absence, presence}", "contrast agent, injection {absence, presence}", a "movement distance to scanning starting position {OO mm or less, OO mm or more}", and "gantry inclination {absence, presence}", illustrated in FIG. 10(b), the scanning preparation control unit 1241 performs a switching process to the "two-person mode" in a case of any one of re-scanning, no plan of scanogram, injection of a contrast agent, a movement distance to a scanning starting position of 500 mm or more, and the presence of an inclination of the gantry.

In a case where setting of a scanning preparation mode set for each part is prioritized, the scanning preparation control unit 1241 automatically selects scanning preparation mode according to the table illustrated in FIG. 10(c). According to the setting in the table illustrated in FIG. 10(c), the scanning preparation control unit 1241 selects the single-person mode in a case where a part is the "chest", and selects the two-person mode in a case where a part is the "abdomen".

In a case where setting of a scanning preparation mode set for each scanning protocol is prioritized, the scanning preparation control unit 1241 automatically selects a scanning preparation mode according to the table illustrated in FIG. 10(d). According to the setting in the table illustrated in FIG. 10(d), the scanning preparation control unit 1241 selects the single-person mode in a case where a scanning protocol is "A", and selects the two-person mode in a case where a scanning protocol is "B".

In "switching checking message display {OFF, ON}" illustrated in FIG. 10(a), it may be designated whether or not a message for checking switching to the designated (the other) mode is displayed. FIG. 10(e) illustrates an example of a checking message. The scanning preparation control unit 1241 allows an operator to select whether or not switching is performed before switching between modes by displaying the checking message.

As a result of employing such a configuration, in the X-ray CT apparatus 1 of the third embodiment, it is possible to cope with a facility where a single person performs examination and a facility where two persons perform examination. It is also possible to cope with both of a facility where it is determined whether a single person performs examination or two persons perform examination depending on the examination content.

As mentioned above, preferred embodiments of the X-ray CT apparatus and the like according to the present invention have been described, but the present invention, is not limited to these embodiments. It is clear that a person skilled in the art can conceive of various modifications or alterations within the scope of the technical spirit disclosed in the present application, and it is understood that they are naturally included in the technical scope of the present invention.

REFERENCE SIGNS LIST

1 X-RAY CT APPARATUS, 1000 SCAN GANTRY PORTION, 1010 X-RAY TUBE, 1020 ROTATION DISK, 1030 COLLIMATOR, 1040 OPENING, 1050 BED, 1060 X-RAY DETECTOR, 1070 DATA COLLECTING DEVICE, 1080 GANTRY CONTROL DEVICE, 1090 BED CONTROL DEVICE, 1100 X-RAY CONTROL DEVICE, 1110 SCAN GANTRY INSTRUCTION DEVICE, 1111 SCAN GANTRY BED MOVEMENT BUTTON, 1112 SCAN GANTRY ROTATION DISK INCLINATION BUTTON, 1113 SCAN GANTRY SCANNING STARTING BUTTON, 1114 SCAN GANTRY STOPPING BUTTON, 1115 SCAN GANTRY SCANNING PREPARATION BUTTON, 1200 OPERATION CONSOLE, 1210 INPUT DEVICE, 1220 IMAGE CALCULATION DEVICE, 1230 STORAGE DEVICE, 1240 SYSTEM CONTROL DEVICE, 1241 SCANNING PREPARATION CONTROL UNIT, 1250 DISPLAY DEVICE, 1260 OPERATION CONSOLE INSTRUCTION DEVICE, 1261 OPERATION CONSOLE BED MOVEMENT BUTTON, 1262 OPERATION CONSOLE SCANNING PREPARATION BOTTOM, 1263 OPERATION CONSOLE SCANNING STARTING BUTTON, 1264 OPERATION CONSOLE STOPPING BOTTOM, 1265 OPERATION CONSOLE SCAN GANTRY SCANNING

PREPARATION BUTTON, 1266 OPERATION CONSOLE SCANNING PREPARATION MODE SWITCHING SWITCH

The invention claimed is:

1. An X-ray CT apparatus comprising:
an X-ray source that irradiates an object with X-rays;
an X-ray detector that is disposed to oppose the X-ray source and detects X-rays having been transmitted through the object;
a rotation disk that is mounted with the X-ray source and the X-ray detector, and is rotated around the object;
an image reconstruction device that reconstructs a tomographic image of the object on the basis of a transmitted X-ray dose detected by the X-ray detector;
an image display device that displays the tomographic image reconstructed by the image reconstruction device;
a system control device that controls the respective devices so as to perform scanning;
an operation console instruction device that instructs the system control device to prepare, start, and stop scanning in an operation console; and
a scan gantry instruction device that instructs the system control device to prepare, start, and stop scanning in a scan room,
wherein the system control device includes a scanning preparation control unit that performs some scanning preparation processes among a plurality of scanning preparation processes on the basis of an instruction for scanning preparation from the operation console instruction device or the scan gantry instruction device.

2. The X-ray CT apparatus according to claim 1,
wherein the scanning preparation control unit controls execution or cancelation of the scanning preparation processes on the basis of the present state which is determined by using two signals generated by operating the operation console instruction device and the scan gantry instruction device, and a scanning preparation control table defining whether or not the scanning preparation processes are performed for each state.

3. The X-ray CT apparatus according to claim 2,
wherein the operation console instruction device includes an operation console scan gantry scanning preparation button which makes a first signal of the two signals ON and an operation console scanning preparation button which makes a second signal which is different from the first signal of the two signals ON, and
wherein an instruction for execution or cancelation of all of the scanning preparation processes is given by using the operation console scan gantry scanning preparation button or the operation console scanning preparation button.

4. The X-ray CT apparatus according to claim 2,
wherein the operation console instruction device includes an operation console scanning preparation mode switching switch that switches between a first mode as a scanning preparation mode in which an instruction for execution or cancelation of ail of the scanning preparation processes is given by operating only the operation console instruction device, and a second mode as a scanning preparation mode in which an instruction for execution or cancelation of all of the scanning preparation processes is given by operating both of the operation console instruction device and the scan gantry instruction device.

5. The X-ray CT apparatus according to claim 4,
wherein the scanning preparation control unit stores a scanning preparation mode switching condition indicating a condition for switching to either the first mode or the second mode in advance, and performs switching to either the first mode or the second mode in a case where the scanning preparation mode switching condition is satisfied.

6. The X-ray CT apparatus according to claim 5,
wherein the scanning preparation control unit allows an operator to select whether or not switching is performed before switching to either the first mode or the second mode.

7. The X-ray CT apparatus according to claim 5,
wherein the scanning preparation mode switching condition is defined by scanning conditions other than a part and a scanning protocol, and
wherein whether or not setting for each part or each scanning protocol is prioritized or whether or not setting of the scanning preparation mode switching condition is prioritized is selected with respect to the scanning preparation mode.

8. A control method for an X-ray CT apparatus including an X-ray source that irradiates an object with X-rays, an X-ray detector that is disposed to oppose the X-ray source and detects X-rays having been transmitted through the object, a rotation disk that is mounted with the X-ray source and the X-ray detector, and is rotated around the object, an image reconstruction device that reconstructs a tomographic image of the object on the basis of a transmitted X-ray dose detected by the X-ray detector, an image display device that displays the tomographic image reconstructed by the image reconstruction device, a system control device that controls the respective devices so as to perform scanning, an operation console instruction device that instructs the system control device to prepare, start, and stop scanning in an operation console, and a scan gantry instruction device that instructs the system control device to prepare, start, and stop scanning in a scan room, the method comprising:
causing the system control device to perform some scanning preparation processes among a plurality of scanning preparation processes on the basis of an instruction for scanning preparation from the operation console instruction device or the scan gantry instruction device.

* * * * *